United States Patent [19]

Finnicum

[11] Patent Number: 5,190,789
[45] Date of Patent: Mar. 2, 1993

[54] ULTRASONIC MONITORING OF A FREELY FLOWING CURTAIN OF COATING MATERIAL

[75] Inventor: Douglas S. Finnicum, Webster, N.Y.

[73] Assignee: Eastman Kodak Company, Rochester, N.Y.

[21] Appl. No.: 751,468

[22] Filed: Aug. 29, 1991

[51] Int. Cl.[5] .................. B05D 1/30; B05C 11/00; B05C 5/00
[52] U.S. Cl. ........................... 427/8; 427/9; 427/10; 427/420; 118/688; 118/324; 118/DIG. 4
[58] Field of Search ............... 118/DIG. 4, 688, 324; 427/420, 9, 10, 8

[56] References Cited

U.S. PATENT DOCUMENTS

| | | | |
|---|---|---|---|
| 3,632,374 | 1/1972 | Greiller | 427/420 |
| 4,019,906 | 4/1977 | Ridley | 427/420 |
| 4,128,667 | 12/1978 | Timson | 427/348 |
| 4,287,240 | 9/1981 | O'Connor | 427/420 |
| 4,419,384 | 12/1983 | Kane et al. | 427/57 |
| 4,463,040 | 7/1984 | Kisler | 427/57 |
| 4,716,058 | 12/1987 | Morin | 427/420 |
| 4,830,887 | 5/1989 | Reiter | 427/420 |
| 4,851,268 | 7/1989 | Kozak | 427/420 |

OTHER PUBLICATIONS

Brochure for "Model M-4000-Ultrasonic Measurement & Control System", Massa Products Corp., 280 Lincoln Street, Hingham, Mass. 02043-1796.
Brochure for "Model E-201A/215-Ultrasonic Ranging Module", Massa Products Corp., 280 Lincoln Street, Hingham, Mass. 02043.
Brochure for "Ultrasonic Proximity Sensors and Systems", L-Tron Associates, 20 N. Main Street, Pittsford, N.Y. 14534.

Primary Examiner—Shrive Beck
Assistant Examiner—Katherine A. Bareford
Attorney, Agent, or Firm—Foley & Lardner

[57] ABSTRACT

A method and apparatus for coating a surface of a continuously moving substrate with a continuously flowing curtain of coating composition comprises transmitting a sound or light wave toward the curtain and detecting the sound or light wave after the transmitting of the sound or light wave. The presence of the curtain is confirmed by either a positive receiving of a reflected sound or light on the smae side of the curtain as the transmitting of the sound or light wave, or a negative receiving of the transmitted sound or light wave on the other side of the curtain. The position of a continuously flowing curtain of coating composition is determined by measuring a time lapse between the time a sound or light wave is transmitted and the time a sound or light wave after reflection from the curtain is received. If the time lapse is outside a predetermined range of a control time period, a signal is generated to indicate that the curtain is defective.

34 Claims, 5 Drawing Sheets

ULTRASONIC MONITORING OF A FREELY FLOWING CURTAIN OF COATING MATERIAL

BACKGROUND OF THE INVENTION

1. Technical Field

The present invention relates generally to a coating system and in particular relates to a method and apparatus for curtain coating a surface. More specifically, the present invention relates to a coating system wherein the physical condition or state of a continuously flowing curtain of coating composition is determined using sound or light pulses or waves.

2. Background Art

Ultrasonic ranging and detection devices utilize high frequency sound waves to measure distances and detect objects. This is done by reflecting high frequency sound waves from objects and by the interruption of high frequency sound waves by an object to be detected. Depending upon the type of sensor that is used, at least one or two transducers are required.

When two transducers are used, one transducer is used as a transmitter to transmit a continuous series of ultrasonic pulses and the second transducer is used as a receiver to receive the transmitted ultrasonic energy. For example, two transducers can be mounted side-by-side and when ultrasonic energy from the transmitter is reflected back from an object, the receiver receives the ultrasonic energy. Some transducers both transmit and receive sonic energy through the same transducer, and with such transducers, only one transducer is required.

Whether one or two or more transducers are used, each transducer is connected to an electronic control module that receives electrical signals from an electronic monitoring module in each transducer and performs predetermined control functions. The control functions are based upon the electrical signals from the electronic monitoring module and include time lapse measurement and distance measurement, as well as other measurement functions.

The speed of ultrasonic energy through a given atmosphere at a relatively constant temperature is a constant. The speed of light, of course, is a constant. Thus, the period of lapsed time between the time an ultrasonic pulse is transmitted and the time a significant reflected ultrasonic pulse or echo is received is a direct function of the distance between the transducer or transducers and the object. This period of lapsed time is used to control an electronic switch or latch. For example, the electronic switch or latch can be set to an "off" position the moment an ultrasonic wave is transmitted, and when a significant echo of the ultrasonic wave is received, the electronic switch can be set to an "on" position. The length of time the electronic switch is in the "off" position can be converted into proportional (or inverted proportional) voltage and current as well as solid state DC on/off switching, depending on the length of time between the transmitting and the receiving of ultrasonic waves.

A transducer may be placed as close as two (2) inches from the object or as far away as sixty (60) inches and further. The level of noise filtration is adjustable using potentiometers, and thus the degree of sensitivity of the receiving transducer can be adjusted in order to effectively predetermine what level of received strength constitutes a significant echo.

Curtain coating methods and apparatus are well-known in the coating field and are widely used for manufacturing photographic films and other thin film coated products. U.S. Pat. No. 3,508,947 to Hughes is directed to a curtain coating method and apparatus for making photographic elements by applying a coating composition onto flexible supports or webs as a free-falling vertical curtain, and discloses the general concept of coating using a curtain of coating composition.

In the curtain coating process, the quality of coating is largely determined by the properties of the liquid curtain. It is critical to insure that a stable laminar flow of liquid film is formed by the slide hopper and that an equally stable, laminar flow liquid curtain is formed from that film To prevent contraction of the falling curtain under the effect of surface tension, it is known that the curtain width must be guided at its edges by curtain edge guides.

Curtain edge guides are generally solid, stationary members that are attached to the slide hopper and extend downwardly from the initial point of free fall of the curtain. Wetting contact of the edges of the falling curtain with the edge guides should be maintained the entire length of the edge guide to avoid a break in the curtain. An edge band liquid can be supplied to the lateral sides of the curtain to stabilize the curtain, and this liquid is collected and recirculated for reuse. U.S. Pat. No. 4,019,906 issued Apr. 26, 1977, discloses a curtain coating process using such edge band liquid techniques.

The edge portions of the film support are customarily embossed by a knurling wheel to increase the effective thickness of the support. The increased thickness of the edge protects the sensitive photographic materials from higher localized winding pressure which occurs as a result of minute variations in support thicknesses. It is desirable to avoid applying any coating compositions to the knurled areas because inherent tackiness of photographic coatings at high humidity makes it difficult to unwind the support during finishing operations. One way of achieving this is to maintain a free falling curtain having a width less than the width of the support. Thus, techniques for providing coating-free margins would be highly useful in connection with edge knurling of the support.

One prior art attempt to maintain the knurled edge portions coating-free has been to locate the edge guides in-board of the edge of the support. However, this causes the coating to terminate along both edges of the support in a bead. Such edges must be cut off to provide a completely uniform coated support. Prior to costly and wasteful trimming operations, however, such excessively thick beads of coating liquid can adversely affect drier efficiency and result in contamination of downstream transport rollers.

Another drawback associated with the curtain coating method is that the air flow adjacent the curtain can cause defective coating layers to be applied onto the supports or webs. It is virtually impossible to render a coating room free of air currents because of the air currents generated by the moving supports or webs. Air currents are further generated by the necessity of having to provide proper ventilation, the necessity of having operating and maintenance personnel enter and exit the coating room, as well as temperature differentials that can cause air currents in the coating room. Such air currents can cause defects in the coating layer, such as non-uniform layers, wrinkles and voids or breaks.

Various slightly redundant attempts have been made to alleviate this problem. For example, in U.S. Pat. No. 4,128,667 to Timson, a stream of gas directed over an air foil situated immediately adjacent a stream of free falling coating fluid is utilized to direct and alter the velocity of the fluid prior to its reaching the web being coated. The air foils guide the stream of gas along the entire width of the fluid stream and act uniformly over the entire length of the stream. In this manner, not only the velocity but the lateral movement of the fluid stream may be controlled. The air foils, however, do not protect the curtain and, in fact, would be damaging to a curtain of photographic emulsion although the damage to plain polymer coatings would be negligible where the character of the emulsion is not sensitive to such damage.

In U.S. Pat. No. 4,287,240 to O'Connor, a shield is provided adjacent the coating zone to protect the flow of coating compositions against disturbance by ambient air currents.

While these attempts have helped to somewhat alleviate the problems caused by disturbances in the ambient air, there still remains the problem that when a disturbance does cause irregular coating of the coating composition layer on the support or web, the defect may go unnoticed until the product reaches quality control check or, sometimes, until the product reaches the end-user.

Under current coating methods and operational parameters, where the web or support is traveling through the coating area at speeds of between one foot per second to several hundreds of feet per second and faster, a defect can be easily missed by simple visual inspection. In the case of continuous voids or gaps in the curtain, hundreds and even thousands of feet of unacceptable and unusable coated support or webbing may be produced before the defect is discovered and corrected. If the defect is discovered, the coating machine must be stopped and the take-up roll must be inspected and unrolled until the beginning point of the defect is reached, with the result that the defective coated support or webbing must be thrown away. This results in losses in terms of lost product and lost production time. If the defect is not discovered, the defective product becomes subject to further investment in terms of downstream processing and packaging, for example, into photographic films, cassette tapes, and other such products, and therefore causes further losses in terms of lost investment. Moreover, if the defective product somehow escapes quality control systems, an end-user may suffer losses as a result of reliance on the defective product.

Under current production schemes, the actual coating speed is limited primarily by the drier capacity. In a typical emulsion curtain coating operation, the coating speed is increased until the drier in the form of a long oven having air flow supports for the emulsion-coated substrates cannot effectively dry the emulsions. In such an operation, it is critical to maintain a proper and consistent coating thickness in order to avoid contaminating downstream rollers as a result of overcoverage of the substrate with emulsion. In such an operation, if the downstream rollers become contaminated with emulsion, hundreds, if not thousands, of feet of coated substrate could become damaged due to adhesion as well as random peeling of the emulsion coating from the substrate. Moreover, the downtime necessary to clean the rollers and other machine parts that have been contaminated with excess emulsion from overcovered substrate results in further substantial losses.

A curtain of coating composition most frequently breaks away from the bottom corner edges of the curtain guides due to the cohesive nature of the composition combined with the acceleration of the curtain as it falls. Occasionally, the curtain will break in the middle due to some compositional imperfection that temporarily breaks the curtain formation. In such a situation, there is almost certain overcoverage of at least certain sections of the substrate with the photographic emulsion. While such overcoverage may only be on a short length of substrate, if undetected, the excess emulsion will either spill off of the substrate or not dry properly and stick to the surface of downstream rollers and contaminate the rollers as well as other mechanical parts and cause the entire coating machine to be shut down for cleaning.

A need has existed for a method and apparatus for coating a surface of a continuously moving substrate with a continuously flowing curtain of coating composition wherein the physical state of the curtain is detected. A need has also existed for a method and apparatus for coating a surface of a continuously moving substrate with a continuously flowing curtain of coating composition wherein the physical presence of the curtain is detected. A further need has also existed for a method and apparatus for coating a surface of a continuously moving substrate with a continuously flowing curtain of coating composition wherein the position of the curtain is determined. Still a further need has existed for a method and apparatus for coating a surface of a continuously moving substrate with a continuously flowing curtain of coating composition wherein physical defects in the curtain are detected. Yet another need has existed for a method and apparatus for coating a surface of a continuously moving substrate with a continuously flowing curtain of coating composition that affords the early detection of physical defects in the curtain to allow effective, corrective action to be taken before such defects cause expensive damage. Another need that has existed is a method and apparatus for coating a surface of a continuously moving substrate with a continuously flowing curtain of coating composition that provides immediate detection of physical defects in the curtain to allow immediate corrective action.

SUMMARY OF THE INVENTION

These and other needs have been satisfied by the invention, as embodied and broadly described herein, that provides a method of coating a surface of a continuously moving substrate with a continuously flowing curtain of coating composition comprising the steps of transmitting successive waves toward the curtain at a predetermined distance from the curtain, receiving the successive waves at a predetermined distance from the curtain after the transmitting of successive waves, and interpreting the successive waves after receiving the successive waves to determine the physical state of the curtain, whereby a signal is generated when the physical state of the curtain exceeds a predetermined range of physical states in order to initiate corrective action.

The present invention further satisfies these needs by providing a method of coating a surface of a continuously moving substrate with a continuously flowing curtain of coating composition comprising the steps of transmitting a wave toward the curtain, reflecting the wave off the curtain and receiving the reflected wave, whereby the presence of the curtain is confirmed by a positive reception of the reflected wave.

The present invention further satisfies these needs by providing a method of coating a surface of a continuously moving substrate with a continuously flowing curtain of coating composition comprising the steps of transmitting a wave toward the curtain from one side of the curtain and receiving the transmitted wave from the other side of the curtain, whereby the presence of the curtain is confirmed by a negative reception of the transmitted wave.

The present invention further satisfies these needs by providing a method of coating a surface of a continuously moving substrate with a continuously flowing curtain of coating composition comprising the steps of transmitting a wave toward the curtain at a predetermined distance from the curtain, reflecting the wave off the curtain, receiving the reflected wave at a predetermined distance from the curtain, measuring a time lapse between the time of transmitting the wave and the time of receiving the reflected wave and determining a curtain position as a function of the time lapse, whereby a signal is generated when the curtain position exceeds a predetermined range of curtain positions in order to initiate corrective action.

The signal generated in the respective methods above may be an electrical signal, a sound signal or a light signal.

The present invention further satisfies these needs by providing an apparatus for coating a surface of a continuously moving substrate with a continuously flowing curtain of coating composition comprising a sound wave transmitting device for transmitting a sound wave toward the curtain, a sound wave receiving device for receiving a reflected sound wave transmitted by the sound wave transmitting device and reflected by the curtain, and an electronic control device operatively associated with the sound wave transmitting device and the sound wave receiving device that determines an actual period of time lapse between the time a sound wave is transmitted and the time a reflected sound wave is received and compares the actual period of time lapse with a control period of time and produces a signal when the actual period of time lapse falls outside a predetermined range of the control period of time to indicate a defective physical condition in the curtain.

By use of the methods and apparatus of the present invention as disclosed and claimed, the physical state of a continuously flowing curtain in a curtain coating apparatus is monitored, and this information can be used to provide feedback information to a computer control system that controls the curtain coating apparatus in order that immediate corrective action can be taken in the event the physical state of the continuously flowing curtain exceeds acceptable ranges of physical states. While it is necessary to use ultrasonic transducers when applying photographic emulsions in order to protect the character of the emulsion itself, it is possible to also use near-infrared light in the form of lasers, and when the character of the emulsion is not subject to damage by light waves other than near-infrared light, then light waves other than near-infrared light in the form of, for example, lasers, may be used.

It is preferable to locate the transmitters/receivers and/or transceivers as close as possible to the point of contact between the curtain of coating composition and the substrate in order that the position and movement of the curtain at points closest to the points of contact may be determined. It is also preferable to locate at least one transmitter/receiver or transceiver adjacent each bottom corner of the curtain of coating composition as close as possible to the corner as possible in order that the slightest break of the curtain from the corner may be detected. Moreover, it is not important which side of the curtain the transmitters/receivers and/or transceivers are located. So long as they are positioned correctly relative to the point of contact of the curtain with the substrate, especially the bottom corners of the curtain, irrespective of which side of the curtain they are positioned, they will provide accurate and useful readings and information.

It is to be understood that both the foregoing general description and the following detailed description are exemplary and explanatory only and are not restrictive of the invention as claimed.

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference will now be made in detail to the present preferred embodiments of the invention, examples of which are illustrated in the accompanying drawings. Wherever possible, the same reference numbers will be used throughout the drawings to refer to the same or like parts. The disclosures and teachings of U.S. Pat. Nos. 3,632,374 and 4,287,240 are hereby incorporated by reference.

Figure 1:
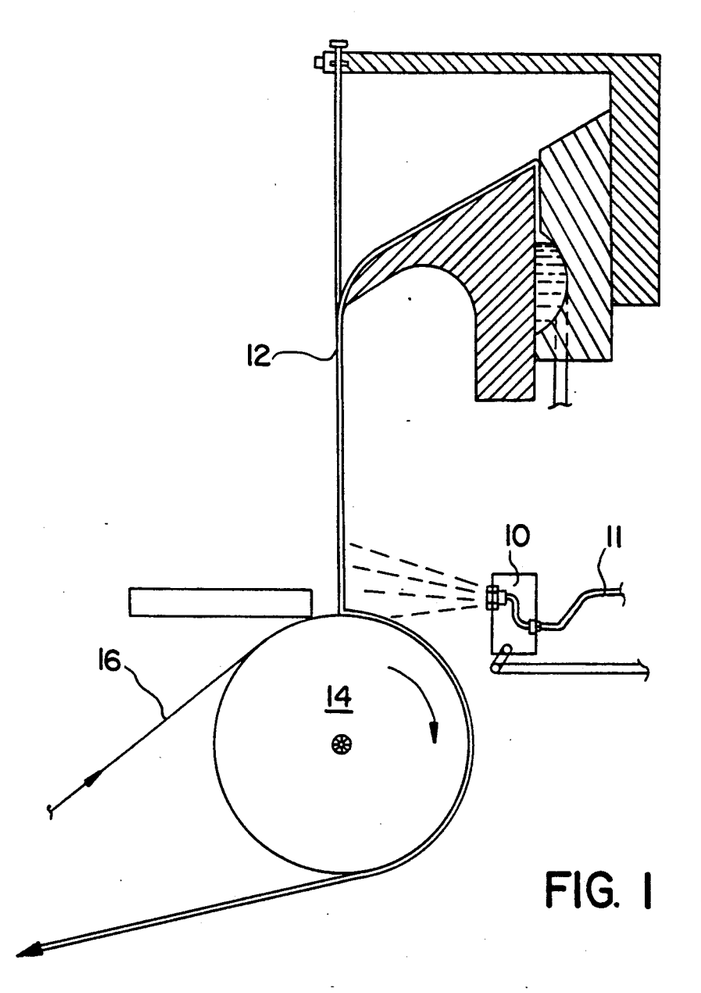
FIG. 1 is a diagrammatic view showing an example of a preferred embodiment of the present invention for detecting the presence of and determining the position of a continuously flowing curtain of coating composition.

Referring now to FIG. 1 and in accordance with the present invention, a transceiver 10 is provided facing a curtain 12 such that no obstruction exists between the transceiver 10 and the curtain 12. The curtain 12 is coated onto web or support 16 as it travels around backing roller 14. The transceiver 10 is both a sound transmitting device and a sound receiving device that transmits ultrasonic waves towards the curtain 12 and receives ultrasonic waves that are reflected off the surface of the curtain 12. This configuration can be referred to as the reflected mode.

The transceiver 10 incorporates an electronic monitoring module (not shown) that can emit an electrical signal to indicate when an ultrasonic pulse or wave is transmitted or received. The electronic monitoring module incorporates adjustable switches and potentiometers that allow selective filtration of stray sonic pulses or waves such as unwanted noise. This permits the sensitivity of the electronic monitoring module to be adjusted to suit the operating conditions and environment so that only those ultrasonic pulses or waves that constitute a significant reflected ultrasonic pulse or wave so as to constitute a significant echo prompt the generation of an electrical signal.

The electronic monitoring module is operatively associated with an electronic control module (not shown) through connection 11. The electronic control module receives the electrical signals generated by the electronic monitoring module and uses these electrical signals to perform predetermined control functions. For example, an actual time lapse between the time an ultrasonic pulse is transmitted and the time a reflected ultrasonic pulse is received can be determined and compared with a control time period or range. If the actual time lapse is either less than or greater than the control time period or range, the electronic control module can be made to generate an electrical signal that can be used in other control functions such as turning on warning signals and/or warning sound alarms or prompting a computer control system controlling the coating operation to stop the coating operation.

Figure 2:
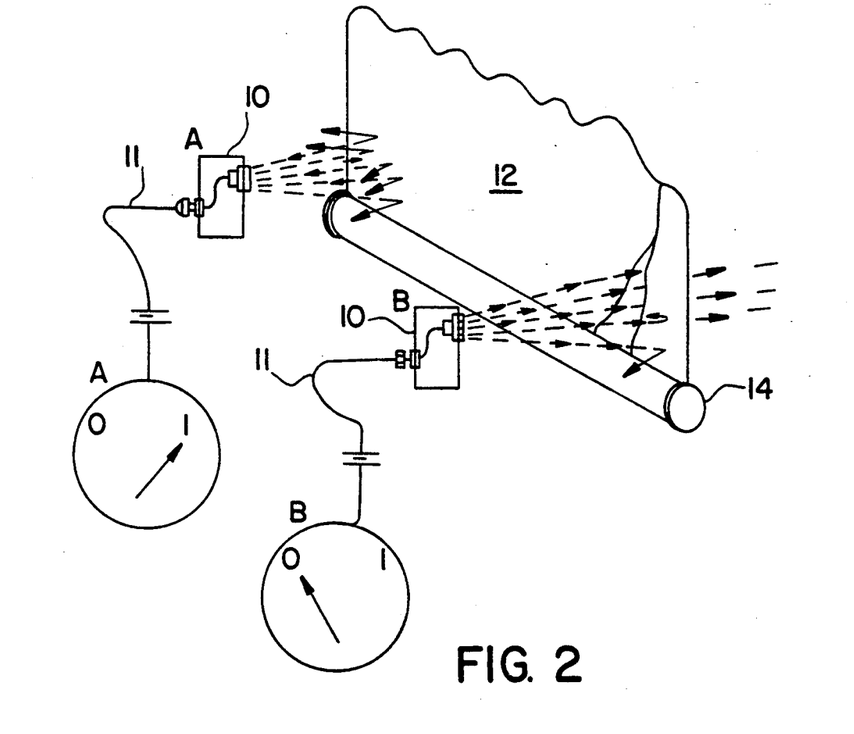
FIG. 2 is a diagrammatic, perspective view showing another embodiment of the present invention for detecting the presence of and determining the position of a continuously flowing curtain of coating composition.
Figure 5:
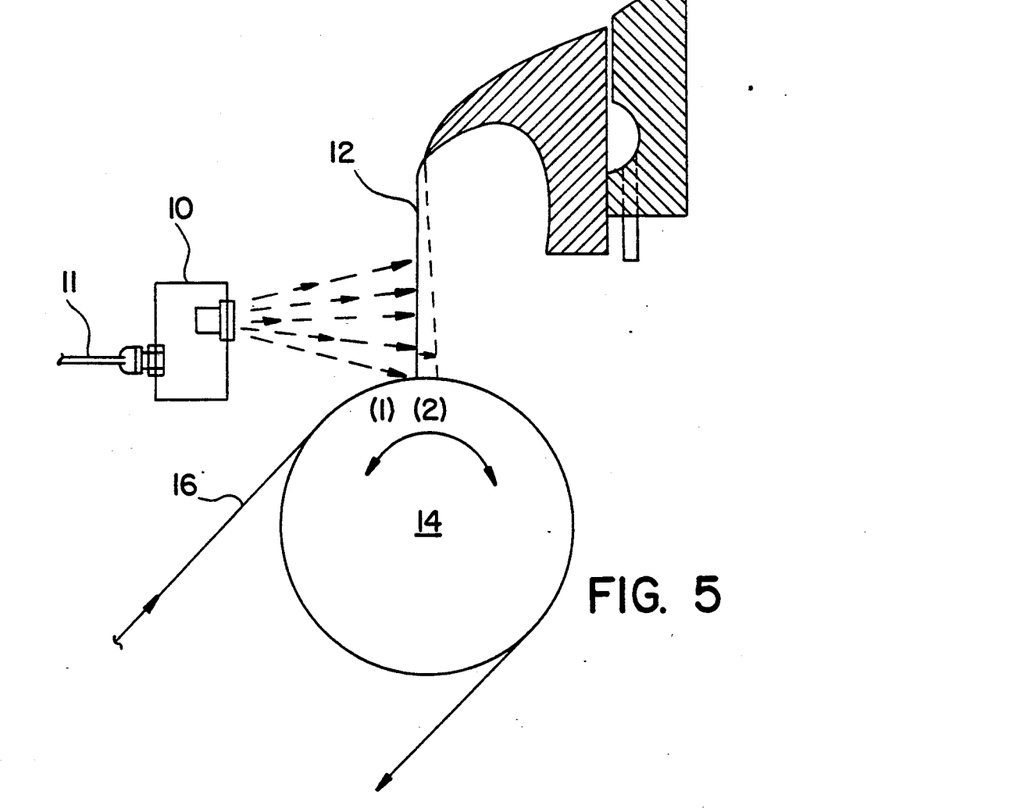
FIG. 5 is a diagrammatic view of an embodiment of the present invention illustrating how the position of the curtain is detected and determined.
Figure 6:
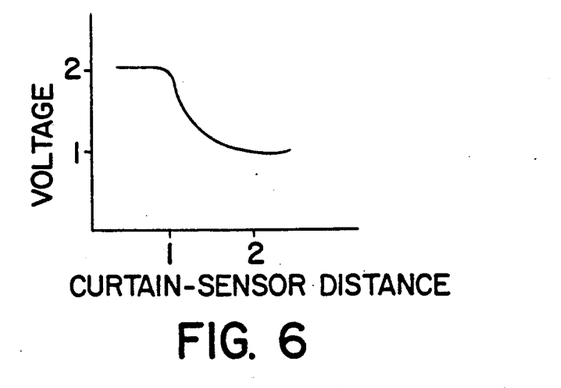
FIG. 6 is a graphical representation of converted voltage readings in a transceiver of reflected sound waves received by the transceiver as the curtain moves from position (1) to position (2) in FIG. 5.
Figure 7:
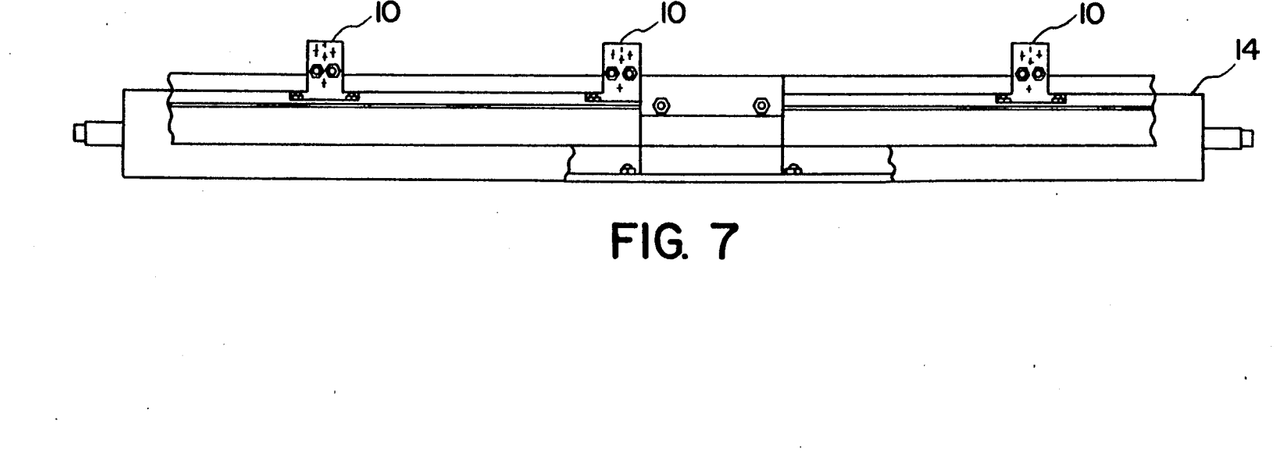
FIG. 7 is a rear diagrammatical view of another preferred embodiment of the present invention showing three transceivers along the length of a coating zone of a curtain coating apparatus.

Referring now to FIGS. 2, 5, and 6, the reflected mode will be further described. In FIG. 2, two transceivers (A) and (B) are mounted facing curtain 12. Transceivers (A) and (B) transmit ultrasonic waves towards the curtain 12 and receive ultrasonic waves that are reflected off the surface of the curtain 12. Transceivers (A) and (B), in conjunction with the electronic monitoring module and the electronic control module, perform the dual function of determining the physical presence of the curtain 12 and determining the position of the curtain 12.

Transceiver (A), as shown in FIGS. 2 and 5, detects the presence of the curtain 12 by detecting the returning ultrasonic waves as they are reflected from the surface of the curtain 12. If the curtain 12 has a break or a parting, there would be no reflected signal for the transceiver to detect. The transceiver 10 (A), in conjunction with the monitoring module and control module, also measures the time lapse between the time of each successive transmission of ultrasonic waves and the time each such successive transmission of ultrasonic waves is received by the transceiver 10 (A) after reflection from the curtain 12.

As shown in FIG. 5, when the curtain 12 is closer to the transceiver 10 (as in position 1), the reflected ultrasonic waves return to the transceiver 10 within a shorter period of time than when the curtain 12 is farther away from the transceiver 10 (as in position 2). The shorter time lapse is translated by the electronic control module into a higher voltage reading as shown on the graph of FIG. 6, whereas the longer time lapse is translated into a lower voltage reading as shown on the graph of FIG. 6. Alternatively, the shorter time lapse may be translated into the lower voltage reading, and the longer time lapse may be translated into the higher voltage reading. The slope of the graph of FIG. 6 is determined by the speed at which the position of the curtain 12 moves from point 1 to point 2. By setting an acceptable range of lateral movement in the forward and rearward directions of the curtain 12 as a function of a selected range of voltage readings, it is possible to detect unacceptable levels of change in the lateral position of the curtain 12 as any voltage reading that either exceeds or falls below the selected range of voltage readings. Any voltage reading that either exceeds or falls below the selected range of voltage readings can be used to generate a signal so that corrective action can be taken.

Additionally, the frequency of the curtain is determined and analyzed by detecting the amount of movement of the curtain over a period of time. If the frequency or regular lateral movement of the curtain exceeds a predetermined frequency range, a warning signal may be generated or the coating operation may be shut off.

Alternatively, the actual time lapse between the time an ultrasonic pulse is transmitted and the reflected ultrasonic pulse is received may be measured using an electronic switch or latch as described above. The length of time the latch is in the off position can be given a numerical value, such as actual time, and this numerical value can be compared with a control number to determine if the numerical value falls outside a predetermined range of the control number. If so, an appropriate signal can be generated in order that corrective action may be taken with respect to the curtain. The generated signal may be a light signal such as a warning light, a sound signal such as a siren or buzzer, or an electrical signal such as an electronic signal or message to a computer, or a combination of such signals.

In the case of transducer 10 (B) shown in FIG. 2, this transducer is shown transmitting ultrasonic waves to a portion of the curtain 12 that is defective due to a void or gap. In this instance, the transmitted ultrasonic waves do not bounce from the curtain 12 but pass through the void or gap. The transceiver 10 (B) does not receive any significant reflected signals and a reflected signal detection dial could indicate "0" to reflect this condition. This condition can be used to generate a signal in much the same manner as described above when an unacceptable level of lateral movement of the curtain generates a signal.

Figure 3:
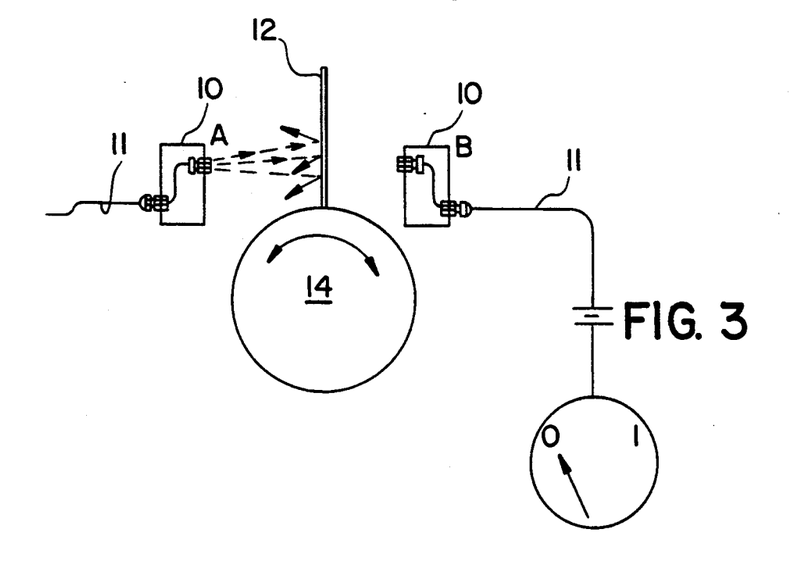
FIG. 3 is a diagrammatic view illustrating a preferred embodiment of the present invention utilizing the transmission mode.
Figure 4:
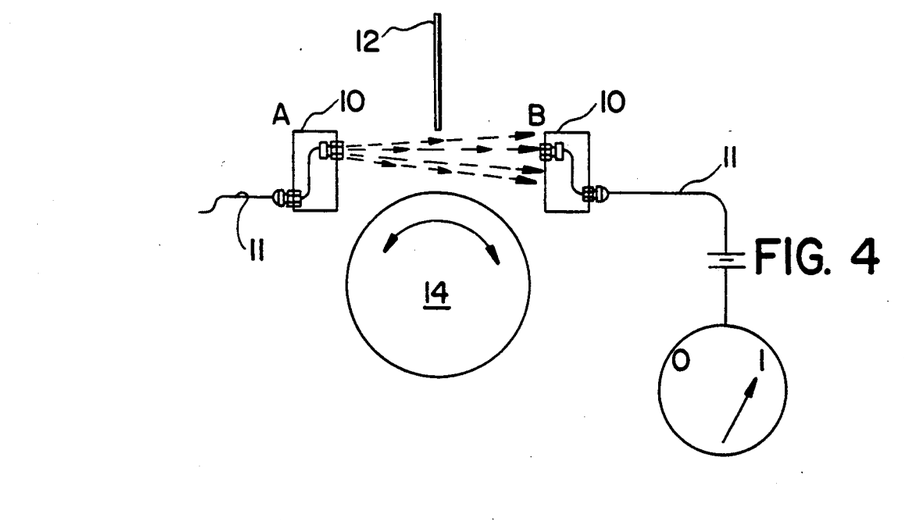
FIG. 4 is a diagrammatic view illustrating another preferred embodiment of the present invention utilizing the reflected mode.

Referring now to FIGS. 3 and 4, a transmission mode will now be described. A transducer 10 is placed on both sides of the curtain 12 facing each other and in near alignment with each other. One transducer (A) is used as a transmitter and the other is used as a receiver (B). The transmitter (A) transmits ultrasonic waves towards the curtain 14. In order to determine the position of the curtain, the transmitter (A), in conjunction with an electronic monitor module and control module, measures the time lapse between the time each successive ultrasonic wave is transmitted and each successively reflected ultrasonic wave is received to determine the actual time lapse and to determine whether the actual time lapse is outside a predetermined range of a control time period. As shown in FIG. 4, however, if there exists a break or void in the curtain, the ultrasonic waves are detected by the transducer (B) on the other side of the curtain. When the transducer/receiver on the other side of the curtain detects ultrasonic waves transmitted by the transmitting transducer (A) on the other side of the curtain, this can be used to generate a signal in much the same manner as when a signal is generated by an actual time lapse that falls outside the predetermined range of the control time period as described above in order to indicate the defect in the curtain.

It is to be noted that the lateral spacing between a transmitter and receiver may be optimized by noting the angle at which the waves are generated and received. Moreover, it is important to also note that the size of the sensor will also contribute to the amount of spacing that will be required.

Alternatively, instead of transmitting sonic waves with a transducer, light waves may be generated and transmitted using appropriate light systems such as a near-infrared light system comprising a light transmitter and a light receiver, laser light systems, and the like. In a reflected mode, again assuming that the light transmitter and light receiver are side-by-side, the closer the curtain 12 is to a light transmitter, the faster the light returns to the light receiver after bouncing from the surface of the curtain 12. Using light systems in the transmission mode would also be useful.

It will be apparent to those skilled in the art that various modifications and variations can be made in the various methods of the present invention and in the construction of the various apparatus of the present invention without departing from the scope or spirit of the invention. As an example, capacitance sensor systems that measure the degree of capacitance as a direct function of movement may be used. Also contemplated are electromagnetic transmitters with receivers.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A method of coating a surface of a continuously moving substrate with a continuously flowing curtain of coating composition comprising the steps of:
   (a) transmitting successive waves toward the curtain at a distance from the curtain;
   (b) receiving the successive waves at a same or different distance from the curtain after step (a); and
   (c) interpreting the successive waves to determine the presence and position of the curtain,
   whereby a signal is generated when either the presence of the curtain is not confirmed or the position of the curtain is outside a range of curtain positions in order to initiate corrective action.

2. A method of coating a surface of a continuously moving substrate with a continuously flowing curtain of coating composition according to claim 1, wherein the successive waves are successive ultrasonic pulses.

3. A method of coating a surface of a continuously moving substrate with a continuously flowing curtain of coating composition according to claim 1, wherein step (a) and step (b) are carried out on one side of the curtain.

4. A method of coating a surface of a continuously moving substrate with a continuously flowing curtain of coating composition according to claim 1, wherein step (a) is carried out on one side of the curtain and step (b) is carried out on both sides of the curtain.

5. A method of coating a surface of a continuously moving substrate with a continuously flowing curtain of coating composition according to claim 1, wherein the wave is a light wave.

6. A method of coating a surface of a continuously moving substrate with a continuously flowing curtain of coating composition according to claim 5, wherein the light wave is a near-infrared light wave.

7. A method of coating a surface of a continuously moving substrate with a continuously flowing curtain of coating composition comprising the steps of:
   (a) transmitting a wave toward the curtain from one side of the curtain;
   (b) reflecting the wave off the curtain; and
   (c) receiving the reflected wave from the same side of the curtain, whereby the presence of the curtain is confirmed by a position reception of the reflected wave.

8. A method of coating a surface of a continuously moving substrate with a continuously flowing curtain of coating composition according to claim 7, wherein the wave is an ultrasonic pulse.

9. A method of coating a surface of a continuously moving substrate with a continuously flowing curtain of coating composition according to claim 7, wherein the wave is a light wave.

10. A method of coating a surface of a continuously moving substrate with a continuously flowing curtain of coating composition according to claim 9, wherein the light wave is a near-infrared light wave.

11. A method of coating a surface of a continuously moving substrate with a continuously flowing curtain of coating composition comprising the steps of:
    (a) transmitting a sound wave toward the curtain from one side of the curtain; and
    (b) receiving the transmitted sound wave from the other side of the curtain,
    whereby the presence of the curtain is confirmed by a negative reception of the transmitted sound wave.

12. A method of coating a surface of a continuously moving substrate with a continuously flowing curtain of coating composition according to claim 11, wherein the sound wave is an ultrasonic pulse.

13. A method of coating a surface of a continuously moving substrate with a continuously flowing curtain of coating composition comprising the steps of:
    (a) transmitting a wave toward the curtain from one side of the curtain at a distance from the curtain;
    (b) reflecting the wave off the curtain;
    (c) receiving the reflected wave from the same side of the curtain at a same or different distance from the curtain;
    (d) measuring the time lapse between the time of transmitting the wave and the time of receiving the reflected wave; and
    (e) determining a curtain position as a function of the length of time lapse,
    whereby a signal is generated when the curtain position exceeds a range of curtain positions in order to initiate corrective action.

14. A method of coating a surface moving substrate with a continuously flowing curtain of coating composition according to claim 13, wherein the wave is an ultrasonic pulse.

15. A method of coating a surface of a continuously moving substrate with a continuously flowing curtain of coating composition according to claim 13, wherein the wave is a light wave.

16. A method of coating a surface of a continuously moving substrate with a continuously flowing curtain of coating composition according to claim 15, wherein the light wave is a near-infrared light wave.

17. An apparatus for coating the surface of a continuously moving substrate with a continuously flowing curtain of coating composition comprising:
 a wave transmitting device for transmitting a wave towards the curtain;
 a wave receiving device for receiving a wave transmitted from the wave transmitting device; and
 an electronic control module operatively associated with the wave receiving device for indicating a condition when the wave receiving device receives a wave transmitted from the wave transmitting device or a condition when the wave receiving device does not receive a wave transmitted from the wave transmitting device,
 wherein the wave transmitting device and the wave receiving device are located on one side of the curtain.

18. An apparatus for coating a surface of a continuously moving substrate with a continuously flowing curtain of coating composition according to claim 17, further comprising a wave receiving device located on the other side of the curtain.

19. An apparatus for coating a surface of a continuously moving substrate with a continuously flowing curtain of coating composition according to claim 17, wherein the wave is a sound wave.

20. An apparatus for coating a surface of a continuously moving substrate with a continuously flowing curtain of coating composition according to claim 19, wherein the sound wave transmitting device comprises an ultrasonic transducer.

21. An apparatus for coating a surface of a continuously moving substrate with a continuously flowing curtain of coating composition according to claim 19, wherein the sound wave receiving device comprises an ultrasonic transducer.

22. An apparatus for coating a surface of a continuously moving substrate with a continuously flowing curtain of coating composition according to claim 19, wherein the sound wave transmitting device and the sound wave receiving device comprises an ultrasonic transceiver.

23. An apparatus for coating a surface of a continuously moving substrate with a continuously flowing curtain of coating composition according to claim 17, wherein the wave is a light wave.

24. An apparatus for coating a surface of a continuously moving substrate with a continuously flowing curtain of coating composition according to claim 23, wherein the light wave is a near-infrared light wave.

25. An apparatus for coating the surface of a continuously moving substrate with a continuously flowing curtain of coating composition comprising:
 a wave transmitting device for transmitting a wave toward the curtain;
 a wave receiving device for receiving a wave transmitted from the wave transmitting device; and
 an electronic control module operatively associated with the wave transmitting device and the wave receiving device for indicating a defective condition in the continuously flowing curtain of coating composition,
 wherein the wave transmitting device and the wave receiving device are located on one side of the curtain.

26. An apparatus for coating a surface of a continuously moving substrate with a continuously flowing curtain of coating composition according to claim 25, further comprising a wave receiving device located on the other side of the curtain.

27. An apparatus for coating a surface of a continuously moving substrate with a continuously flowing curtain of coating composition according to claim 25, wherein the wave is a sound wave.

28. An apparatus for coating a surface of a continuously moving substrate with a continuously flowing curtain of coating composition according to claim 27, wherein the sound wave transmitting device comprises an ultrasonic transducer.

29. An apparatus for coating a surface of a continuously moving substrate with a continuously flowing curtain of coating composition according to claim 27, wherein the sound wave receiving device comprises an ultrasonic transducer.

30. An apparatus for coating a surface of a continuously moving substrate with a continuously flowing curtain of coating composition according to claim 27, wherein the sound wave transmitting device and the sound wave receiving device comprise an ultrasonic transceiver.

31. An apparatus for coating a surface of a continuously moving substrate with a continuously flowing curtain of coating composition according to claim 25, wherein the wave is a light wave.

32. An apparatus for coating a surface of a continuously moving substrate with a continuously flowing curtain of coating composition according to claim 31, wherein the light wave is a near-infrared light wave.

33. An apparatus for coating a surface of a continuously moving substrate with a continuously flowing curtain of coating composition according to claim 25, wherein the electronic control module determines an actual period of time lapse between the time a sound wave is transmitted and the time a reflected sound wave is received and compares the actual period of time lapse with a control period of time and produces a signal when the actual period of time lapse falls outside a predetermined range of the control period of time to indicate a defective physical condition in the curtain.

34. An apparatus for coating a surface of a continuously moving substrate with a continuously flowing curtain of coating composition according to claim 33, wherein the signal produced by the electronic control module is a light signal, a sound signal, an electrical signal or a combination thereof.

* * * * *

UNITED STATES PATENT AND TRADEMARK OFFICE
CERTIFICATE OF CORRECTION

PATENT NO. : 5,190,789
DATED : March 2, 1993
INVENTOR(S) : Douglas S. FINNICUM

It is certified that error appears in the above-identified patent and that said Letters Patent is hereby corrected as shown below:

Title page,
item [57] ABSTRACT, col. 2, line 8, delete "smae" and insert --same--.

Column 2, line 13, after "film" insert --.--.

Claim 7, line 9, delete "position" and insert

--positive--.

Signed and Sealed this

Eleventh Day of January, 1994

*Attest:*

BRUCE LEHMAN

*Attesting Officer*    *Commissioner of Patents and Trademarks*